United States Patent
Chou

(10) Patent No.: US 7,754,136 B2
(45) Date of Patent: Jul. 13, 2010

(54) METHOD FOR MANUFACTURING SURFACE ACOUSTIC WAVE DEVICE

(75) Inventor: Tai-Hsu Chou, Taipei Hsien (TW)

(73) Assignee: Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 0 days.

(21) Appl. No.: 12/347,262

(22) Filed: Dec. 31, 2008

(65) Prior Publication Data

US 2009/0289395 A1    Nov. 26, 2009

(30) Foreign Application Priority Data

May 21, 2008    (CN)    ........................ 2008 1 0301711

(51) Int. Cl.
*B29C 35/08* (2006.01)
(52) U.S. Cl. ........................ 264/496; 264/139; 264/319; 310/308; 310/309; 310/311
(58) Field of Classification Search ................. 264/319, 264/496, 139; 310/308, 309, 311
See application file for complete search history.

(56) References Cited

U.S. PATENT DOCUMENTS

| | | | |
|---|---|---|---|
| 5,113,115 A * | 5/1992 | Mariani ................... 310/313 D |
| 5,972,568 A * | 10/1999 | Seniuk et al. ............... 430/312 |
| 6,516,665 B1 * | 2/2003 | Varadan et al. .......... 73/504.01 |
| 6,517,995 B1 * | 2/2003 | Jacobson et al. ............ 430/320 |
| 2004/0007799 A1 * | 1/2004 | Choi et al. .................. 264/494 |
| 2004/0257906 A1 * | 12/2004 | Scriba et al. ................ 366/127 |
| 2006/0043626 A1 * | 3/2006 | Wu et al. ..................... 264/101 |
| 2007/0154349 A1 * | 7/2007 | Kimura et al. ................ 422/57 |
| 2007/0159027 A1 * | 7/2007 | Tsai et al. ............... 310/313 R |
| 2008/0087554 A1 * | 4/2008 | Norris et al. ................ 205/792 |

\* cited by examiner

*Primary Examiner*—Joseph S Del Sole
*Assistant Examiner*—David N Brown, II
(74) *Attorney, Agent, or Firm*—Clifford O. Chi

(57) ABSTRACT

A method for manufacturing a surface acoustic wave device comprises depositing a detecting material layer on a substrate, forming a predetermined pattern on the detecting material layer using a nanoimprint method to obtain a detecting film with a predetermined pattern formed thereon, and forming an input interdigital transducer and an output interdigital transducer on two opposite sides of the detecting material layer on the substrate, thus obtaining a surface acoustic wave device comprising the detecting film.

20 Claims, 6 Drawing Sheets

METHOD FOR MANUFACTURING SURFACE ACOUSTIC WAVE DEVICE

BACKGROUND

1. Technical Field

The disclosure relates generally to a method for manufacturing a surface acoustic wave device.

2. Description of Related Art

Surface acoustic wave devices utilize electromechanical conversion and rely on surface acoustic waves that propagate elastic energy, concentrated on the surface of a solid. Generally, a surface acoustic wave device is provided with an input interdigital transducer (IDT), an output IDT and a detecting film on a piezoelectric substrate. The detecting film is positioned between the two IDTs. Each IDT includes a pair of comb-shaped electrodes interdisposed with each other.

The detecting film absorbs adjacent gas molecules or liquid molecules. When an electrical signal is applied to the input IDT, the piezoelectric substrate is stressed, creating a surface acoustic wave. The surface acoustic wave passes through the substrate and is transmitted to the output IDT, at which point the acoustic wave signal is converted to an electric signal for output. Absorption of the detecting film increases mass thereof. When the surface acoustic wave passes through the substrate, because of mass loading effect on the detecting film, an excursion occurs in phase velocity and attenuation of the output signal. The molecular concentration of the gas or liquid to be detected can be read from the excursion.

The detecting film, generally formed on the substrate via Chemical Vapor Deposition (CVD), may exhibit an uneven surface with only limited area for detection.

Therefore, a method for manufacturing a surface acoustic wave device is needed that can overcome the limitations described.

BRIEF DESCRIPTION OF THE DRAWINGS

The components in the drawing are not necessarily drawn to scale, the emphasis instead being placed upon clearly illustrating the principles of the present disclosure.

Figure 1:
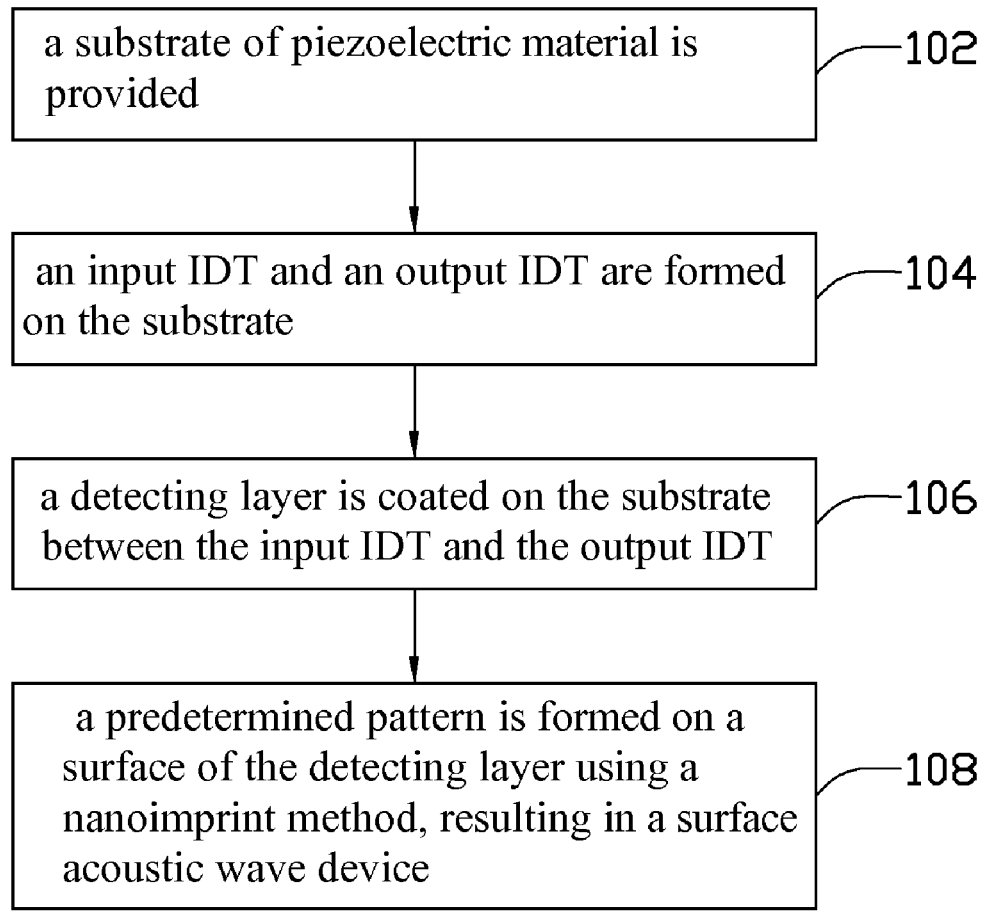
FIG. 1 is a flowchart of a method for manufacturing a surface acoustic wave device.
Figure 2:
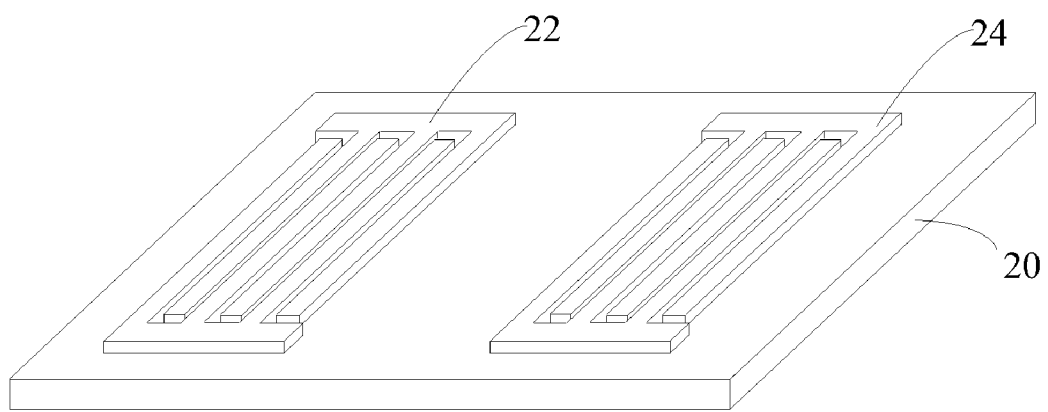
FIG. 2 is a schematic, isometric view of a substrate with two IDTs thereon.

Corresponding reference characters indicate corresponding parts. The exemplifications set out herein illustrate at least one present embodiment of the present method for manufacturing a surface acoustic wave device, in one form, and such exemplifications are not to be construed as limiting the scope of the disclosure in any manner.

DETAILED DESCRIPTION OF THE EMBODIMENTS

Reference will now be made to the drawings to describe embodiments of the present method for manufacturing a surface acoustic wave device in detail.

Referring to FIG. 1, a method for manufacturing a surface acoustic wave device includes Step 102, in which a substrate of piezoelectric material is provided. In Step 104, an input IDT and an output IDT are formed on the substrate. In Step 106, a detecting layer is coated on the substrate between the input IDT and the output IDT. In Step 108, a predetermined pattern is formed on a surface of the detecting layer using a nanoimprint method, resulting in a surface acoustic wave device.

Referring to FIGS. 2 to 5, a method for manufacturing a surface acoustic wave device according to a first embodiment is detailed as follows. In step 102, a rectangular substrate 20 is provided. The substrate 20 is piezoelectric material such as single crystal, such as quartz, $LiNbO_3$, and $LiTaO_3$, thin film specie, such as AlN, or ZnO; ceramic species, such as barium titanate, lead zirconate-titanate, or polymer such as polyvinylidene fluoride.

In step 104, an input IDT 22 and an output IDT 24 are formed on a surface of the substrate 20 by micro-etching or micro-electromechanical process.

Figure 3:
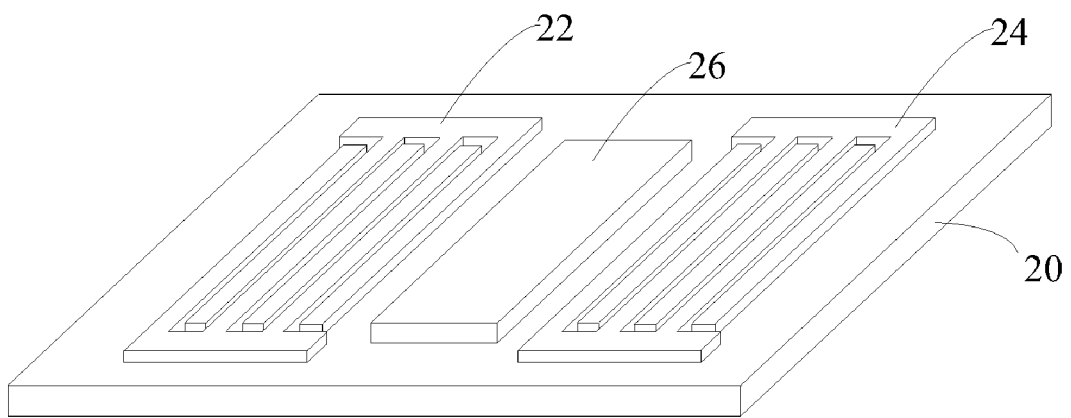
FIG. 3 is a schematic, isometric view showing a substrate with two IDTs and a detecting material layer thereon.

Referring to FIG. 3, in step 106, a detecting layer 26 is formed on the substrate 20 between the input IDT 22 and the output IDT 24 by glow discharge, magnetron sputtering, radiofrequency sputtering, reactive sputtering, or cyclotron wave sputtering.

Material of the detecting layer 26 may be ZnO, to detect ultraviolet radiation, ZnO or Pd to detect hydrogen gas, or $SnO_2$ to detect carbon monoxide.

Figure 4:
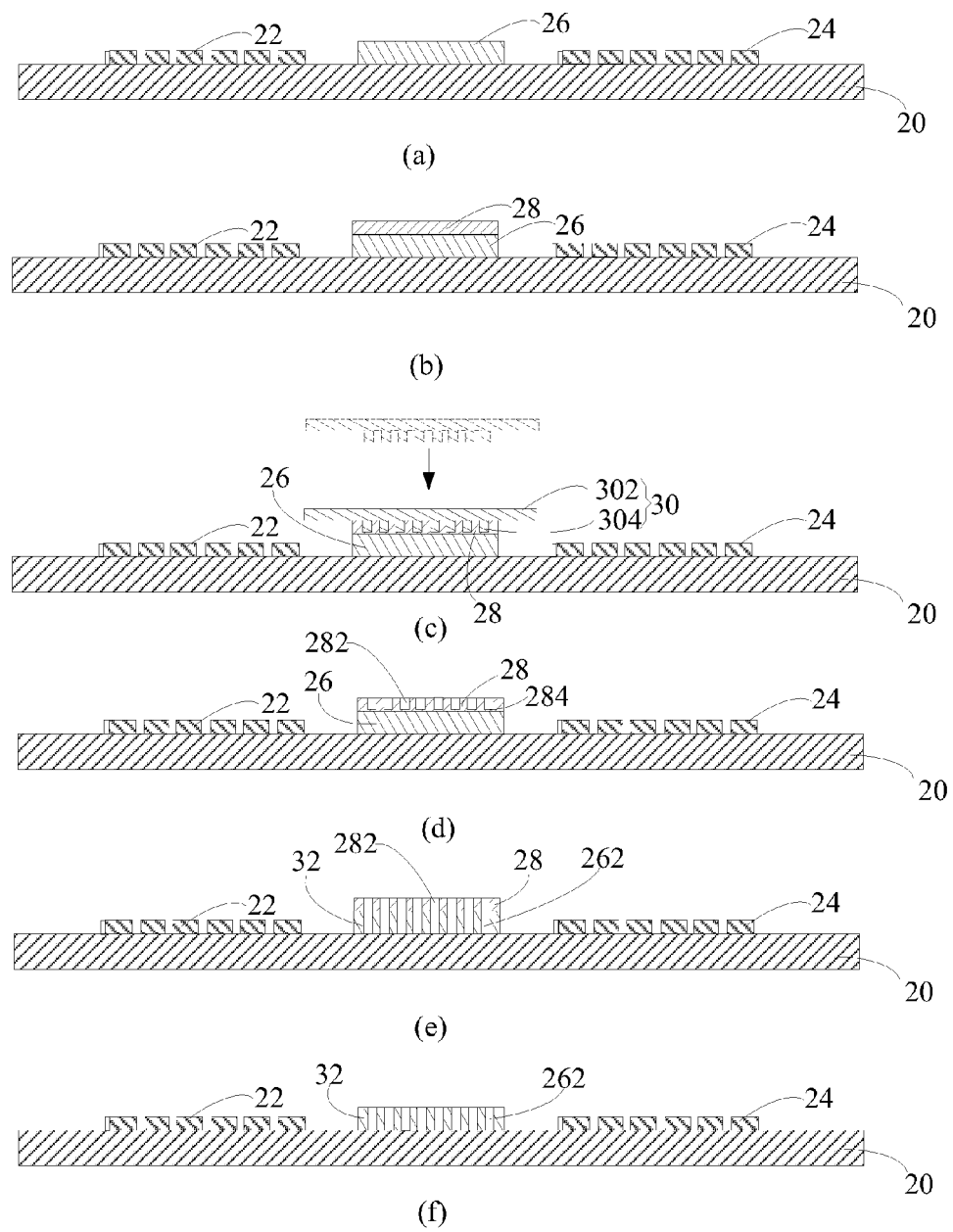
FIG. 4 shows a method for forming a detecting film on the substrate according to a first embodiment.

Referring to FIG. 4, in step 108, a predetermined pattern is formed on a surface of the detecting layer 26 using nanoimprinting. In this embodiment, hot pressing forms the predetermined pattern, detailed as follows.

Referring to FIGS. 4(*a*) and 4(*b*), a polymer layer 28 is deposited on a surface of the detecting layer 26. The polymer layer 28 is heated beyond a glass transition temperature of the polymer layer 28, whereby the polymer layer 28 is softened. The temperature must be prevented from rising too high, otherwise time required for solidifying the polymer layer 28 will be increased. In this embodiment, the polymer layer 28 is polymethyl methacrylate (PMMA). A glass transition temperature of the PMMA is 104° C., thus the temperature for heating the polymer layer 28 may be from 105° C. to 110° C.

Referring to FIG. 4(*c*), a mold 30 is provided. The mold 30 includes a base 302 and a plurality of protrusions 304 of a predetermined shape. The plurality of protrusions 304 is arranged on a surface of the base 302 and integrally connected with the base 302. The mold 30 is of a material exhibiting maximum hardness, compression strength, and tension strength, to prevent distortion and abrasion thereof. In addition, the mold 30 should demonstrate high heat conductivity and low thermal expansion coefficient. Material for mold 30 can be silicon, silicon oxide, silicon nitride, or diamond, with required dimensions of the protrusions 304 accurate to about 10 to 100 nanometers (nm).

The protrusions 304 face polymer layer 28, and are pressed thereinto, forming compressed regions.

Referring to FIG. 4(*d*), the polymer layer 28 is cooled to solidify and the mold 30 removed. The protrusions 304 pressed into the polymer layer 28 do not contact the detecting layer 26. Thus, a plurality of recesses 282 are formed at the compressed regions which generally conform to the profile of the protrusions 304. A thin polymer layer 284 remains between each recess 282 and the detecting layer 26.

The thin polymer layer 284 of the polymer layer 28 between the recess 282 and the detecting layer 26 is removed, thereby exposing the detecting layer 26. Removal may be effected utilizing any appropriate process such as reactive ion etching, wet chemical etching or other. The predetermined pattern of the protrusions 304 is transfer printed onto the detecting layer 26 using the polymer layer 28 as a mask, by etching or stripping. As shown in FIG. 4(e), after selectively etching the detecting layer 26, a plurality of holes 262 are defined in the detecting layer 26.

Figure 5:
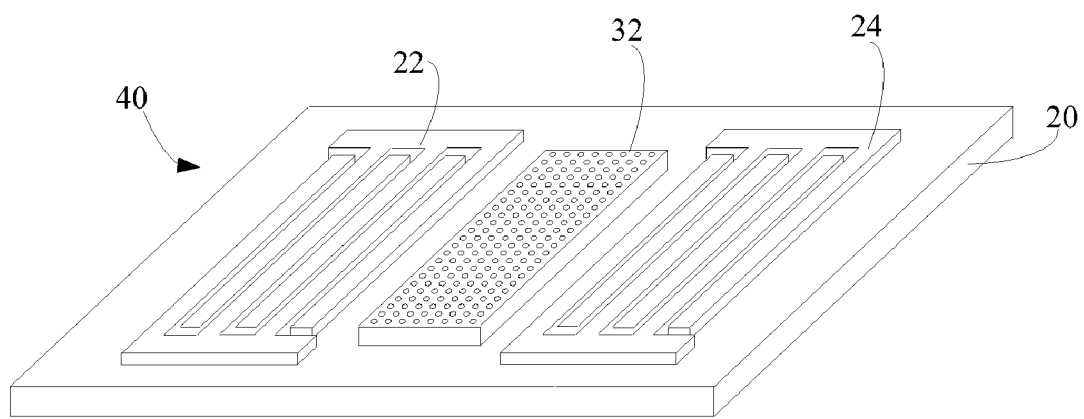
FIG. 5 is a schematic, isometric view showing a surface acoustic wave device formed by the method in FIG. 4.

As shown in FIGS. 4(f) and 5, the remaining polymer layer 28 is removed, leaving a detecting film 32 with predetermined pattern on the surface thereof, with the surface acoustic wave device 40 subsequently obtained. Here, the predetermined pattern is a plurality of holes 262 conforming to the protrusions 304.

It is to be understood that formation of the input IDT 22 and the output IDT 24 can be interchanged in the process with formation of the detecting film 32.

Figure 6:
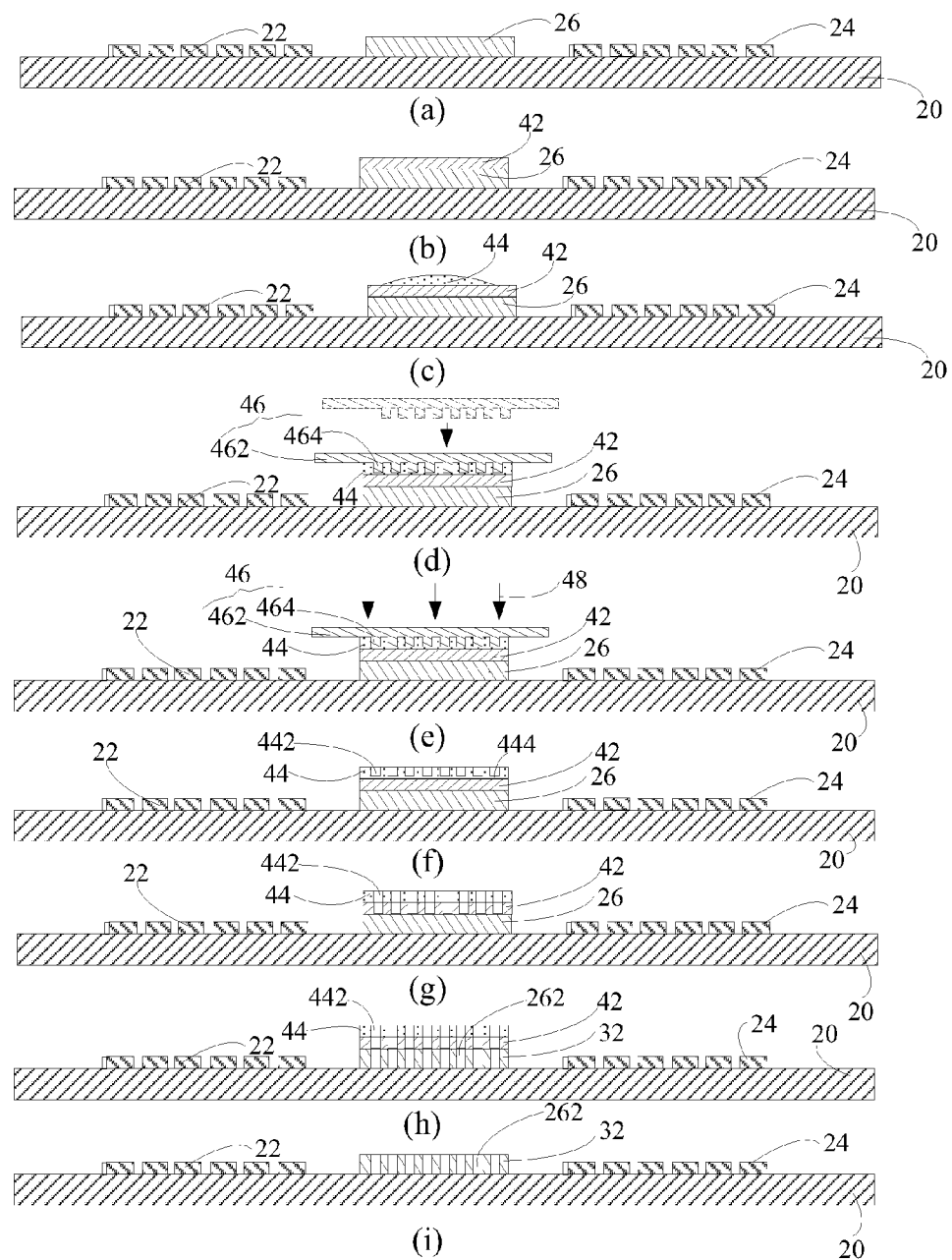
FIG. 6 shows a method for forming a detecting film on the substrate according to a second embodiment.

Referring to FIG. 6, a method for forming a predetermined pattern on a surface of a detecting layer 26 according to another embodiment is provided, in which an organic interlayer 42 is deposited on the surface of the detecting layer 26. The organic interlayer 42 is PMMA and here, the organic interlayer 42 is deposited on the detecting layer 26 by spin coating.

Referring to FIG. 6(c), an imprinted layer 44 is deposited on the organic interlayer 42. The imprinted layer 44 can be a polymer or an organic solution having characteristics of fluidity at room temperature and curable by ultraviolet light. Here, the imprinted layer 44 is organic silicon solution.

Referring to FIGS. 6(d) and 6(e), a mold 46 is provided. The mold 46 includes a base 462 and a plurality of protrusions 464 of a predetermined shape. The plurality of protrusions 464 is arranged on and integrally connected with a surface of the base 462. The mold 46 can be quartz glass or polydimethylsiloxane, with dimensions of the protrusions 304 accurate to 20 nm to 100 nm.

The protrusions 464 face the imprinted layer 44, and are pressed thereinto, forming compressed regions.

Ultraviolet light 48 is applied, irradiating and solidifying the imprinted layer 44, after which the mold 46 is removed. As shown in FIG. 6(f), the protrusions 464 pressed into the imprinted layer 44 do not contact the organic interlayer 42, resulting in a plurality of recesses 442 formed at the compressed regions generally conforming to the profile of the protrusions 464. A thin imprinted layer 444 remains between each recess 442 and the organic interlayer 42.

Referring to FIGS. 6(g) and 6(h), the thin imprinted layer 444 of the imprinted layer 44 between the recess 442 and the organic interlayer 42 and the exposed part of the organic interlayer 42 are removed, exposing the detecting layer 26. Removal can utilize any appropriate process such as reactive ion etching or wet chemical etching. The predetermined pattern of the protrusions 464 is transfer printed onto the detecting layer 26 using the imprinted layer 44 and the organic interlayer 46 as a mask, by etching or a stripping. After etching of the detecting layer 26, a plurality of holes 262 conforming to the protrusions 464 are defined in the detecting layer 26.

Referring to FIG. 6(i), the remaining imprinted layer 44 and the organic interlayer 42 are removed, resulting in a detecting film 32 with a predetermined pattern on the surface thereof.

The detecting film 32 formed by the nanoimprint method, having a predetermined nanometer-sized pattern, provides a large area making contact with the substance to be detected, increasing detecting precision and efficiency. In addition, the nanoimprint method presents a simplified process suitable for mass production.

Finally, it is to be understood that the described embodiments are intended to illustrate rather than limit the disclosure. Variations may be made to the embodiments without departing from the spirit of the disclosure as claimed. The above-described embodiments illustrate the scope of the disclosure but do not restrict the scope of the disclosure.

What is claimed is:

1. A method for manufacturing a surface acoustic wave device, comprising:
   depositing a detecting material layer on a substrate;
   forming a predetermined pattern on the detecting material layer using a nanoimprint method, thus obtaining a detecting film with a predetermined pattern formed thereon; and
   forming an input interdigital transducer and an output interdigital transducer at two opposite sides of the detecting film on the substrate, thus obtaining a surface acoustic wave device comprising the detecting film, each of the two opposite sides being a side of the detecting film that is farthest from the other of the two opposite sides.

2. The method as claimed in claim 1, wherein the nanoimprint method is a hot pressing nanoimprint method or an ultraviolet nanoimprint method.

3. The method as claimed in claim 1, wherein a material of the detecting material layer is selected from the group consisting of ZnO, Pd and $SnO_2$.

4. The method as claimed in claim 2, wherein the hot pressing nanoimprint method comprises:
   depositing a polymer layer on the detecting material layer;
   heating the polymer layer to soften the polymer layer;
   providing a mold, the mold comprising a base and a plurality of nano-scale protrusions formed on the base, the plurality of nano-scale protrusions forming the predetermined pattern;
   pressing the nano-scale protrusions into the polymer layer;
   solidifying the polymer layer;
   removing the mold to form a plurality of recesses in the polymer layer;
   defining a plurality of holes in the detecting material layer according to the pattern of the recesses in the polymer layer; and
   removing the remaining polymer layer, thus obtaining a detecting film with the predetermined pattern formed thereon on the substrate.

5. The method as claimed in claim 4, wherein a material of the polymer layer is polymethyl methacrylate.

6. The method as claimed in claim 5, wherein the polymethyl methacrylate polymer layer is heated to a temperature in a range from 105° C. to 110° C.

7. The method as claimed in claim 4, wherein the predetermined pattern is transferred to the detecting material layer by etching or stripping.

8. The method as claimed in claim 2, wherein the ultraviolet nanoimprint method comprises:
   depositing an organic interlayer on the detecting material layer;
   coating an imprinted layer on the organic interlayer, the imprinted layer being fluid at room temperature and ultraviolet-curable;
   providing a mold, the mold comprising a base and a plurality of nano-scale protrusions formed on the base, the plurality of nano-scale protrusions forming the predetermined pattern;
   pressing the nano-scale protrusions into the imprinted layer;

applying ultraviolet light to irradiate and solidify the imprinted layer;

removing the mold to form a plurality of recesses in the imprinted layer;

defining a plurality of holes in the detecting material layer according to the pattern of the recesses in the imprinted layer; and removing the remaining organic interlayer and the imprinted layer, thus obtaining a detecting film with the predetermined pattern formed thereon on the substrate.

9. The method as claimed in claim 8, wherein the imprinted layer comprises an organic silicon solution.

10. The method as claimed in claim 8, wherein the predetermined pattern is transferred to the detecting material layer by etching or stripping.

11. A method for manufacturing a surface acoustic wave device, comprising:

providing a substrate;

forming an input interdigital transducer and an output interdigital transducer at two opposite sides of a major surface of the substrate, each of the two opposite sides being a side of the substrate that is farthest from the other of the two opposite sides;

depositing a detecting material layer on the major surface of the substrate between the input interdigital transducer and the output interdigital transducer; and forming a predetermined pattern on the detecting material layer using a nanoimprint method, thus obtaining a detecting film with a predetermined pattern formed thereon;

thus obtaining a surface acoustic wave device comprising the detecting film.

12. The method as claimed in claim 11, wherein the nanoimprint method is a hot pressing nanoimprint method or an ultraviolet nanoimprint method.

13. The method as claimed in claim 11, wherein a material of the detecting material layer is selected from the group consisting of ZnO, Pd and $SnO_2$.

14. The method as claimed in claim 12, wherein the hot pressing nanoimprint method comprises:

depositing a polymer layer on the detecting material layer;

heating the polymer layer to soften the polymer layer;

providing a mold, the mold comprising a base and a plurality of nano-scale protrusions formed on the base, the plurality of nano-scale protrusions forming the predetermined pattern;

pressing the nano-scale protrusions into the polymer layer;

solidifying the polymer layer;

removing the mold to form a plurality of recesses in the polymer layer;

defining a plurality of holes in the detecting material layer according to the pattern of the recesses in the polymer layer; and removing the remaining polymer layer, thus obtaining a detecting film with the predetermined pattern formed thereon on the substrate.

15. The method as claimed in claim 14, wherein a material of the polymer layer is polymethyl methacrylate.

16. The method as claimed in claim 15, wherein the polymethyl methacrylate polymer layer is heated to a temperature in the range from 105° C. to 110° C.

17. The method as claimed in claim 14, wherein the predetermined pattern is transferred to the detecting material layer by one of etching and stripping.

18. The method as claimed in claim 12, wherein the ultraviolet nanoimprint method comprises:

depositing an organic interlayer on the detecting material layer;

coating an imprinted layer on the organic interlayer, the imprinted layer being fluid at room temperature and ultraviolet-curable;

providing a mold, the mold comprising a base and a plurality of nano-scale protrusions formed on the base, the plurality of nano-scale protrusions forming the predetermined pattern;

pressing the nano-scale protrusions into the imprinted layer;

applying ultraviolet light to irradiate and solidify the imprinted layer;

removing the mold to form a plurality of recesses in the imprinted layer;

defining a plurality of holes in the detecting material layer according to the pattern of the recesses in the imprinted layer; and removing the remaining organic interlayer and the imprinted layer, thus obtaining a detecting film with the predetermined pattern formed thereon on the substrate.

19. The method as claimed in claim 18, wherein the imprinted layer comprises an organic silicon solution.

20. The method as claimed in claim 18, wherein the predetermined pattern is transferred to the detecting material layer by etching or stripping.

* * * * *